United States Patent [19]

Radke

[11] 4,344,441
[45] Aug. 17, 1982

[54] MANDIBULAR ELECTROMYOGRAPH

[75] Inventor: John C. Radke, Seattle, Wash.

[73] Assignee: Myo-Tronics Research, Inc., Seattle, Wash.

[21] Appl. No.: 165,794

[22] Filed: Jul. 3, 1980

[51] Int. Cl.³ ............................................. A61B 5/04
[52] U.S. Cl. .................................................. 128/733
[58] Field of Search .............................. 128/639–644, 128/733; 328/145

[56] References Cited

U.S. PATENT DOCUMENTS

| 3,448,289 | 6/1969 | Harris | 328/145 |
| 3,657,646 | 4/1972 | Zmyslowski et al. | 128/733 |
| 3,736,515 | 5/1973 | Kadron et al. | 328/145 |
| 3,942,516 | 3/1976 | Glynn et al. | 128/733 |

OTHER PUBLICATIONS

Johansson, S. et al., "An Automated Method for the Frequency Analysis of Myoelectric Signals Evaluated by an Investigation of the Spectral Changes Following Strong Sustained Contractions", Med. & Biol. Eng., V 8, #3, pp. 257–264, 1970.
Costa, P. F. et al., "Multi-Channel Data Acquisition System for the Survey of Intercostal Muscle Activity", Med. & Biol. Eng. & Computing, Jul. 1980, V 18, pp. #447–455.
Geister, D. E. et al., "Computerized Data Acquisition & Analysis for Real-Time EMG in Clinical Dentistry", Proc. IEEE, vol. 63, #10, Oct. 1975.

Primary Examiner—Kyle L. Howell
Assistant Examiner—Francis J. Jaworski
Attorney, Agent, or Firm—Seed, Berry, Vernon & Baynham

[57] ABSTRACT

A system for measuring and displaying the coordination, duration of and interval between contractions of the masticatory muscles. Several electrodes, each associated with a masticatory muscle, generate signals responsive to muscle contraction. The electrode outputs are amplified, rectified and filtered, and then applied to several circuits, depending upon the operating mode selected. In a first mode, the filtered outputs are integrated during each muscle contraction and displayed by an electronic bar graph. The output is also applied to a threshold circuit which identifies the start and finish of the muscle contraction. The output of the threshold circuit is then processed by a timing circuit which determines and displays in digital form the duration of the muscle contraction and the interval between contractions. The system operates in a second mode in the same manner as in the first mode, except that an analog signal is derived from the digitized interval signal and applied to the bar graph in place of the integrated output. In a third mode, the filtered output is applied to a logarithmic amplifier which drives the bar graph so that the logarithm of the electrode voltage amplitude is displayed. The output of the threshold circuit is also processed by a second timing circuit which determines and displays in digital form the time lapse between the contraction of the first muscle to contract and the contraction of the remaining muscles, thereby providing an indication of muscle coordination.

20 Claims, 8 Drawing Figures

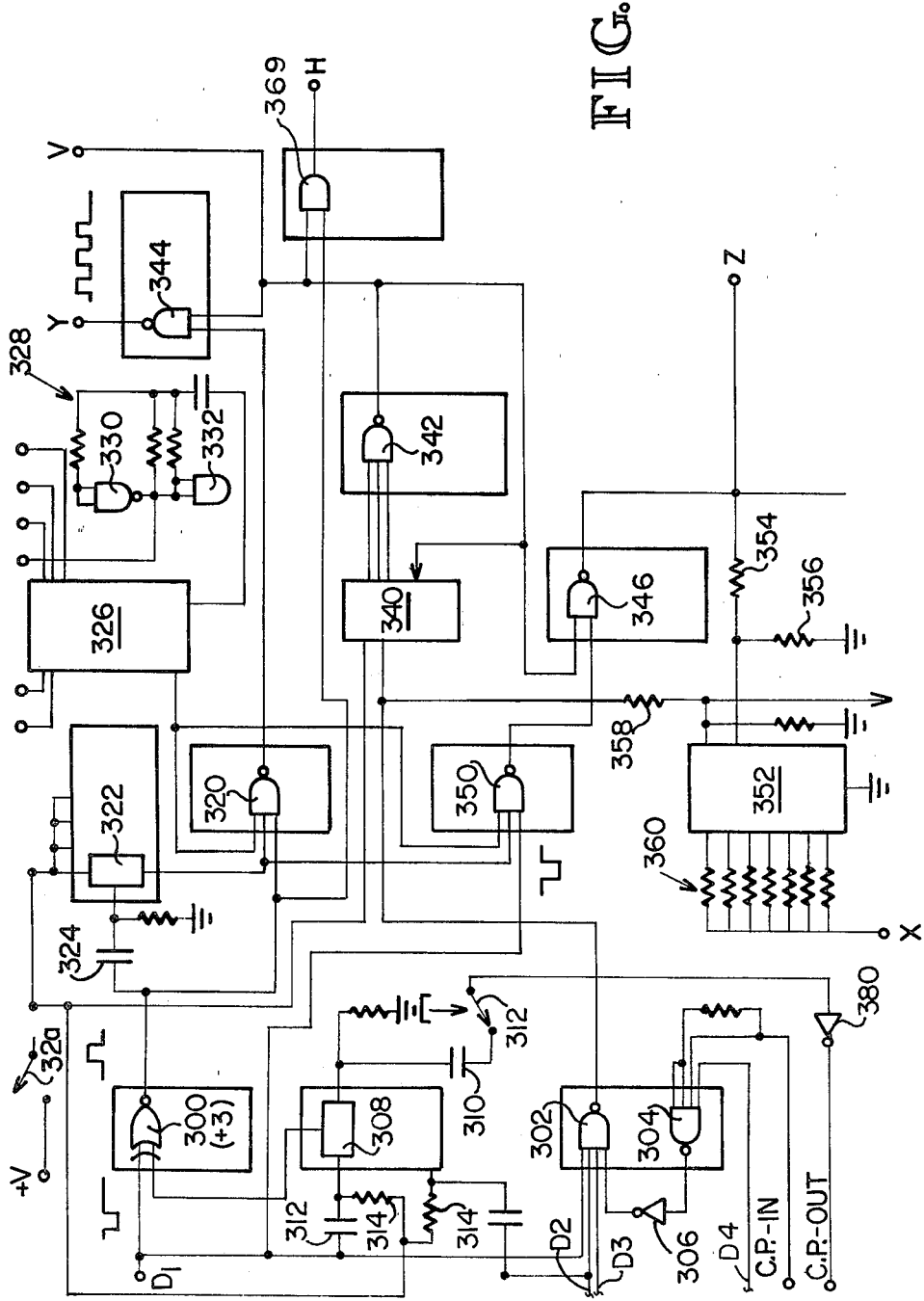

MANDIBULAR ELECTROMYOGRAPH

BACKGROUND OF THE INVENTION

1. Field of the Invention

This invention relates to dental instrumentation devices, and more particularly, to a mandibular electromyograph for measuring and displaying various comparisons of timing and amplitude characteristics of the masticatory muscles.

2. Description of the Prior Art

Electromyographs utilize conventional electrodes placed on the surface of the skin to pick up electric potentials generated by contraction of the muscles beneath the skin. Electromyographs have long been used in the medical and dental fields for a variety of purposes, including the examination of masticatory muscles for pathological conditions. The masticatory muscles are muscles of the human body which produce mandibular movement associated with chewing.

Although mandibular electromyographs have been previously used, their use is limited by the difficulty of interpreting the information thereby obtained. In the conventional mandibular electromyograph, the electric potentials from the electrodes are amplified, filtered, and then usually applied directly to the X axis of an oscilloscope or strip chart recorder. The characteristics of a single masticatory muscle are examined by measuring the spacing of various portions of the electrode signal on the oscilloscope screen or strip chart. The accuracy of this technique is inherently limited by the resolution of rulers or scales printed on the strip chart. Furthermore, it requires a great deal of concentration by the practitioner administering the test. The characteristics of masticatory muscle contractions can only be compared to the contractions of other masticatory muscles with a great deal of difficulty. Such comparisons are traditionally made by simultaneously displaying two, four, or more channels, each containing an electrode output, on the oscilloscope or strip chart at the same time. Use of this technique is even more difficult with an oscilloscope since it is extremely difficult to simultaneously examine multiple traces on the oscilloscope screen. This technique is used with strip chart recorders by manually drawing transverse lines across the strip chart and comparing the recording for each channel with the line. The line drawing and comparing process is, of course, slow and tedious.

As a result of the foregoing disadvantages, mandibular electromyographs have not achieved widespread acceptance for clinical use, but instead, have remained a laboratory tool or a device used by relatively few practitioners.

SUMMARY OF THE INVENTION

It is an object of the invention to provide an electromyograph for graphically comparing the contraction characteristics of a masticatory muscle with the contraction characteristics of other masticatory muscles.

It is another object of the invention to measure and display a variety of characteristics of masticatory muscle contraction.

It is another object of the invention to allow the outputs of several masticatory muscles to be displayed in a manner which makes the pathological condition of one muscle readily apparent.

It is still another object of the invention to provide an electromyograph device which inherently provides measurements of high accuracy.

It is still another object of the invention to provide a zero-offset, full-wave rectifier for rectifying the amplitude and filtered output of a masticatory muscle signal in a linear manner.

It is a further object of the invention to provide a logarithmic circuit for accurately providing an indication of the logarithm of the output from an electrode.

These and other objects of the invention are provided by an electromyograph for measuring and displaying electrical signals from a plurality of electrodes positioned to receive signals from respective masticatory muscles. One portion of the electromyograph device includes respective threshold circuits for generating actuating signals when the amplitude of the electrode outputs are larger than a predetermined value. The actuating signals are enabled at the start of any one of the actuating signals and are disabled at the start of the actuating signal from the threshold circuit of the electrode with which the timer is associated. The count in the timer for each electrode is displayed, thereby providing accurate indications of the elapsed time between contraction of the first-to-contact masticatory muscle and the contraction of the remaining masticatory muscles. This provides a graphic and accurate measurement of muscle coordination. The output of the threshold circuit may also be used to enable a switch which applies the signals from the electrode to an integrator during muscle contractions. The output of the integrator is displayed, thereby providing an indication of the amplitude of the muscle contraction. The integration preferably occurs during several muscle contractions to provide an indication of average muscle contraction intensity. The output of the threshold circuit may also be processed by a timing circuit which determines and displays the duration of each muscle contraction as well as the interval between two muscle contractions. The electromyograph preferably uses a full-wave rectifier having rectifying diodes which are biased at the threshold of conduction so that they instantly respond to an input signal. The output of the full-wave rectifier is thus a linear function of its input. The logarithmic circuit, which the electromyograph preferably uses, is an operational amplifier having a diode connected in its feedback path so that the current through the diode, and hence the output voltage of the amplifier, are equal to the current through a summing resistor and thus proportional to the input voltage. A constant voltage may be added to the output of the operational amplifier so that the resulting voltage is proportional to the logarithm of the input voltage for all ranges.

BRIEF DESCRIPTION OF THE DRAWINGS

FIG. 5 is a schematic of the digital processing circuitry for the electromyograph.

DETAILED DESCRIPTION OF THE INVENTION

Figure 1:
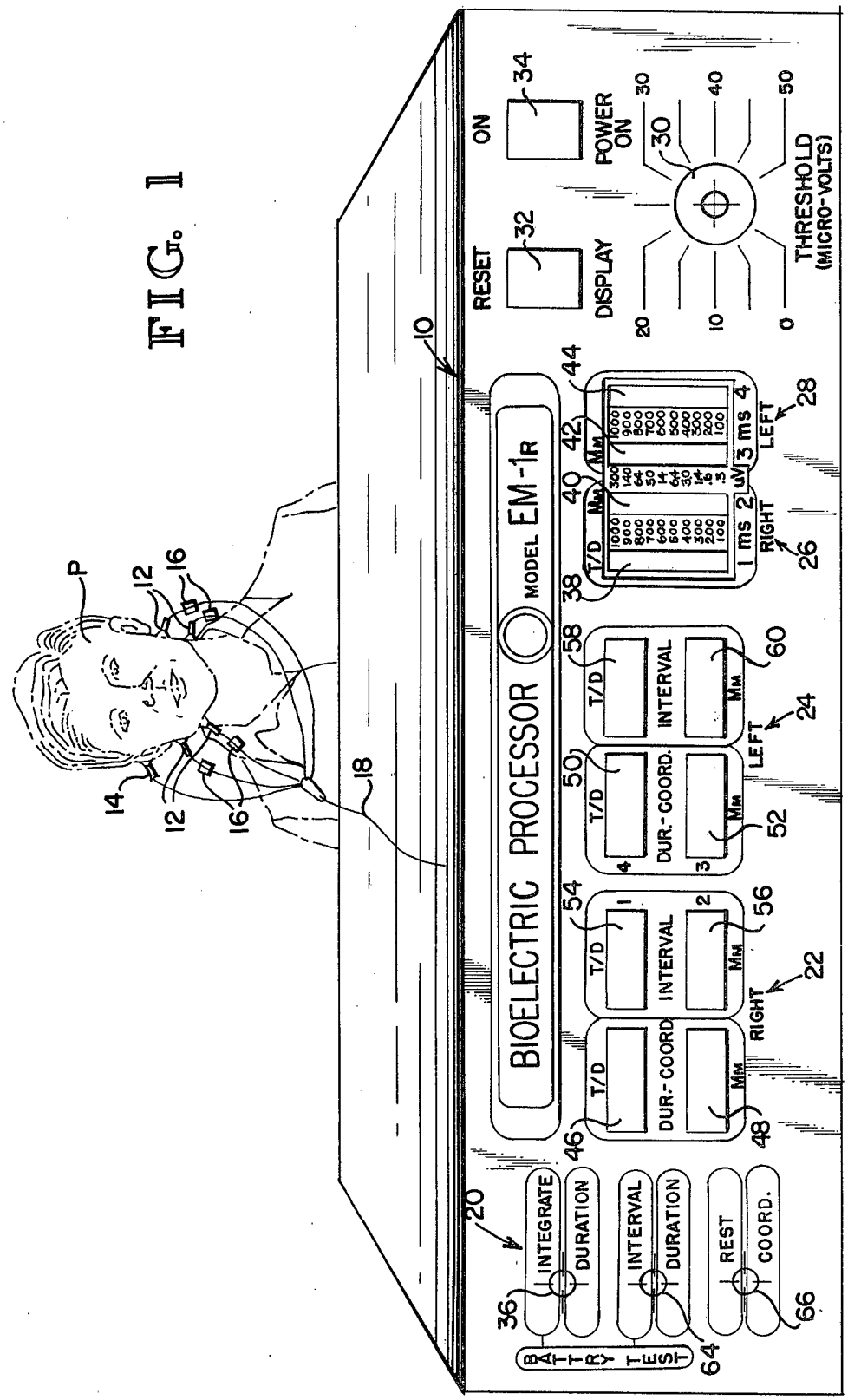
FIG. 1 is an isometric view of the electromyograph in use for measuring the activity of masticatory muscles.

The electromyograph device 10 is illustrated in use in FIG. 1 to measure and display characteristics of the masticatory muscles of a patient P. Four bipolar electrodes 12 of conventional design are secured to the skin of the patient at the proper location to pick up electric signals generated by contraction of the masticatory muscles. In actuality, there are eight muscles of interest; namely, two masseter muscles, two posterior temporalis muscles, two anterior temporalis muscles, and two diagnostic muscles, located under the chin of the patient P. A reference electrode 14 connected to circuit ground is secured to the earlobe of the patient P. Since there are eight potential electrode locations and the outputs of only four electrodes may be processed by the electromyograph, the electrodes 12 are generally used in either of two combinations. The electromyograph can receive signals from electrodes secured to all four locations on one side of the patient's face to pick up signals from masticatory muscles on that side. Alternatively, the electrodes 12 can be positioned to receive signals from the masseter muscles and either the anterior or posterior temporalis muscles on both sides of the patient's face.

Each electrode 12, other than the reference electrode 14, is connected to a low-noise differential preamplifier 16 which boosts the amplitude of the signal picked up by the electrodes 12, thereby achieving a high signal-to-noise ratio. The outputs of the amplifiers 16 are routed to the electromyograph 10 through a multiconductor cable 18.

The electromyograph 10 includes a set of function switches 20, a pair of right and left digital readouts 22,24, respectively, a pair of right and left electronic bar graphs 26,28, respectively, a threshold adjusting knob 30, a combination reset/display switch 32, and a power-on switch 34. The threshold adjusting knob 30 is used to select a level from the output of the electrodes 12 which corresponds to a muscle contraction to allow time-related characteristics of the contraction to be determined and displayed.

In the first operating mode, the switch 36 is pressed, and the amplitude of each preamplifier output is filtered, amplified, rectified, and then integrated over several muscle contractions. The integrated output for each electrode 12 is then displayed on the respective bar graphs 38,40,42,44 for the four electrodes 12. The amplified, filtered and rectified signals are also applied to a threshold circuit which is processed by a timer to determine the average contraction duration over a large number of contractions which are displayed by the respective digital readouts 46,48,50,52 for the four electrodes 12. The average interval between contractions during a large number of contractions is also displayed by respective digital readouts 54,56,58,60 for the four electrodes 12.

In operation, the reset switch 32 is deflected upwardly to remove the previously recorded indications from pairs of displays 22,24,26,28. The reset switch 32 is then deflected downwardly to turn on the digital displays.

A second mode is selected by pressing the switch 64. The information provided by the digital readouts 46-60 in the second mode is the same as in the first mode. However, in the second mode, the bar graphs 38-44 also provide an indication of the interval between contractions during a large number of contractions.

A third mode is selected by pressing switch 66. In this mode, the amplified, filtered and rectified signals from the electrodes 12 are each applied to a logarithmic circuit which generates an output which is the logarithm of its input. The outputs of the logarithmic circuits are applied to the respective bar graphs 38,40,42,44. The digital readouts 54,56,58,60 continue to display the interval between contractions during a large number of contractions. However, the digital readouts 46,48,50,52 are used to provide an indication of muscle coordination. Accordingly, the outputs of all four threshold circuits are continuously examined. A clock signal is applied to a counter for each electrode 12 when the threshold circuit for any of the electrodes 12 produces an output. Thus the first-to-contract masticatory muscle causes the counters for all masticatory muscles to begin incrementing. The counters continue incrementing until the threshold circuit associated with each counter produces an output indicative of masticatory muscle contraction. The system thus measures the elapsed time from contraction of the first-to-contract masticatory muscle to the contraction of the remaining masticatory muscles. Consequently, the digital readout for the first-to-contract masticatory muscle provides a "zero" readout, while the remaining digital readouts 46-52 will provide an indication of the time delay from contraction of the first-to-contract masticatory muscle.

Figure 2:
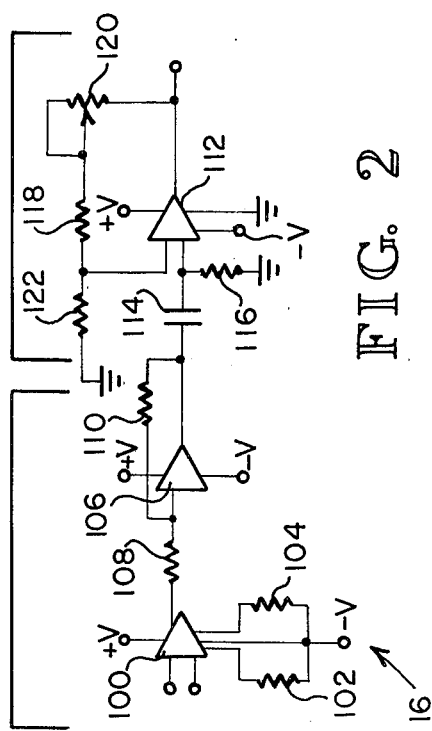
FIG. 2 is a schematic of the preamplifier for the electromyograph.

A schematic of the preamplifier 16 for the mandibular electromyograph is illustrated in FIG. 2. The preamplifiers 16 include a conventional differential amplifier 100 having a high input impedance and low noise characteristics. The gain of the amplifier is set by resistors 102,104 to approximately 100. The output of the amplifier 100 is a differential current which is proportional to the differential input voltage. This differential current is applied directly to the non-inverting input of low-noise operational amplifier 106 and to the summing junction of amplifier 106 through resistor 108. A feedback resistor 110 connected between the summing junction and the output of the amplifier 106 controls the gain of the amplifier 106. The output of amplifier 106 is applied to the non-inverting input of a second operational amplifier 112 through capacitor 114. A resistor 116, connected between the non-inverting input and ground along with the capacitor 114, sets the frequency response break-point of the amplifier at approximately 3 Hz so that frequencies below the break-point, such as motion artifact and offsets, are substantially attenuated. The gain of the amplifier 112 is set by the ratio of the series resistance of resistor 118 and potentiometer 120 to the resistance of resistor 122 to be about 100.

Figure 6:
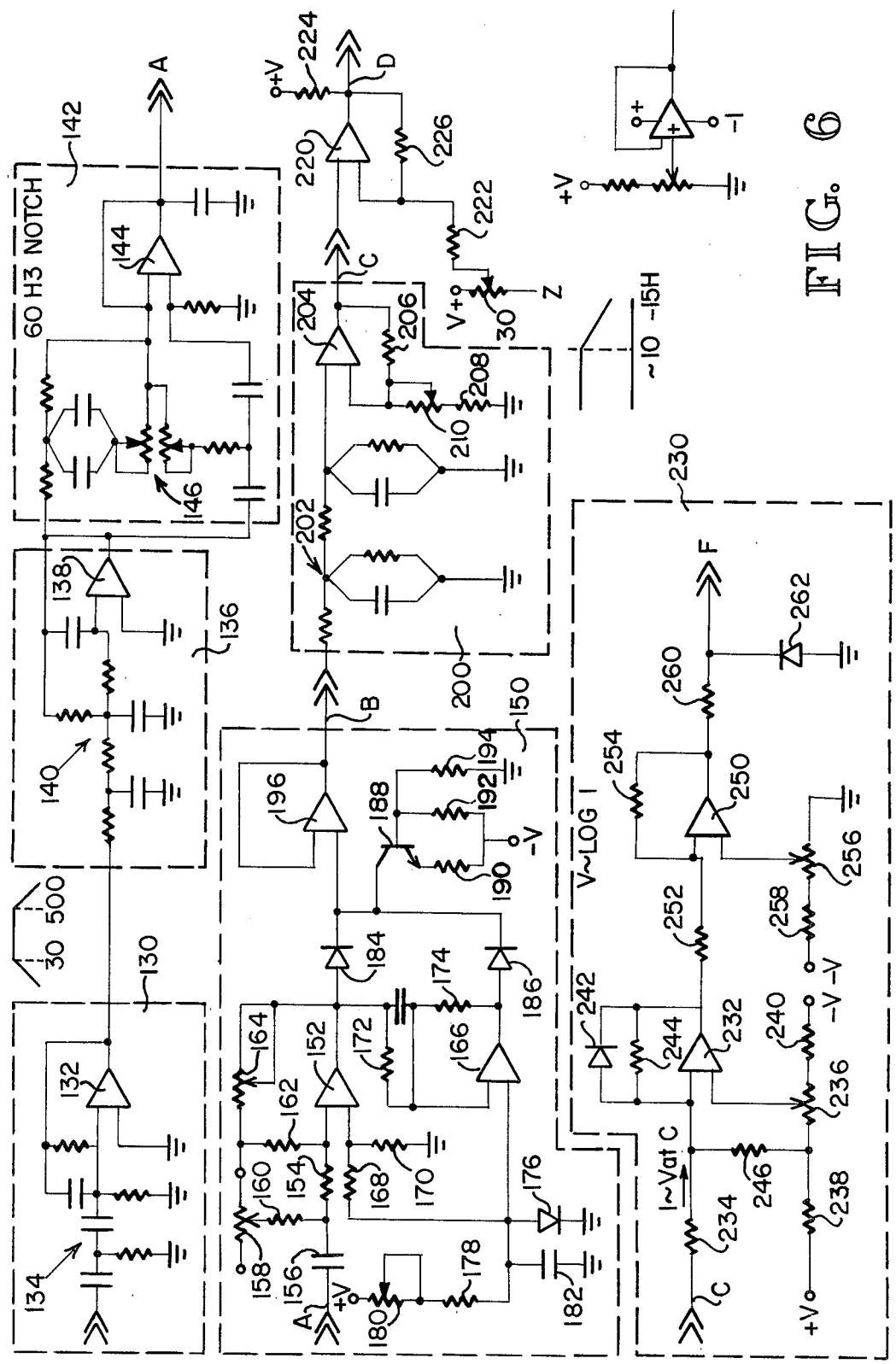
FIG. 6 is a schematic of the analog processing circuitry for the electromyograph.

The output of the preamplifier 16 is applied to a high-pass filter 130 illustrated in FIG. 6. The filter 130 is formed by an operational amplifier 132 and a conventional resistor-capacitor network 134. The frequency break-point of the filter 130 is approximately 30 Hz.

The output of high-pass filter 130 is applied to a low-pass filter 136, also formed by an operational amplifier 138 and a conventional resistor-capacitor network 140. The low-pass filter 136 may have a frequency break-point of approximately 500 Hz.

The output of the low-pass filter 136 is applied to a 60 Hz notch filter 142, also utilizing an operational amplifier 144 and a conventional resistor-capacitor network 146. The notch filter 142 removes 60-cycle signals which are picked up by the electrodes 12 and wiring from 60 Hz power consuming devices. The output of the filter 142 is identified for future reference as signal "A" and it is applied to a variety of points in the electromyograph.

The output "A" of the filter 142 is applied to a unique zero-offset, full-wave rectifier 150. The signal "A" is applied to the summing junction of an operational amplifier 152 through resistor 154 and a bypass capacitor 156. A potentiometer 158 is adjusted to bias the circuit through resistor 160 so that the junction of capacitor 156 and resistor 154 at zero volts. This adjustment causes the operation of the rectifier 150 to be symmetrical for positive and negative inputs, as explained hereinafter. The gain of the amplifier 52 is set by resistor 162 and potentiometer 164 to be slightly greater than unity to make up for losses occuring in the previously described circuit. The non-inverting input of amplifier 152 is connected to a second operational amplifier 166 through resistor 168. Resistor 170, approximately equal in value to resistor 168, is provided to reduce the offset of amplifier 152. The output of amplifier 152 is applied to the summing junction of amplifier 166 through resistor 172, and feedback resistor 174 sets the gain of amplifier 166 at approximately unity.

A diode 176 is connected to the non-inverting input of amplifier 166, and current flows through the diode 176 from resistor 178 and potentiometer 180. The potentiometer 180 is adjusted, as explained hereinafter, so that the rectifier 150 responds to extremely low input voltages so that there is no deadband in the response characteristics of the circuit 150. Capacitor 182 maintains the current through diode 176 relatively constant. The cathodes of a pair of diodes 184,186 are connected to each other, and their anodes are connected to the outputs of amplifiers 152,166, respectively. A constant current drain formed by transistor 188 and resistors 190, 192 and 194 causes a constant total current to flow through diodes 184,186.

In operation, potentiometer 180 is adjusted so that the voltage drop across diode 176 is equal to the voltage drop across diodes 184,186. The high gain of amplifier 166 causes the differential voltage between the inputs of amplifier 166 to approach zero. Consequently, the voltage applied to the summing junction of amplifier 166 is virtually equal to the voltage drop across diode 176. Since the current flowing into the summing junction of 166 is then substantially zero, the outputs of amplifiers 152 and 166 are also equal to the voltage drop across diode 176. Insofar as diode 184 and 186 are forward biased by the current through transistor 188, the voltage at the cathodes of the diodes 184,186 is zero volts. Thus, when a negative voltage from notch filter 142 is applied to the rectifier 150, the output of amplifier 152 goes positive, and this positive voltage is applied to voltage-follower amplifier 196 through diode 184. Since the diode 184 is already conducting before the signal is applied to the rectifier 150, the rectifier 150 responds instantly to the input signal as it begins decreasing. A positive input signal produces a negative output from amplifier 152 which back-biases diode 184 and produces a positive output from amplifier 166. The positive output of amplifier 166 is coupled through diode 186 to the amplifier 196. The zero-offset, full-wave rectifier 150 thus does not produce non-linear distortions in the signal from the notch filter 142. The output of the full-wave rectifier, identified for future reference as signal "B," is positive, but it is composed primarily of high-frequency components. Consequently, the output signal is applied to a low-pass filter 200 which includes a conventional resistor-capacitor network 202 connected to the non-inverting input of operational amplifier 204. Resistors 206,208 and potentiometer 210 are used to provide the amplifier 204 with sufficient gain to compensate for the loss in the resistor-capacitor network 202. The output of the filter 200 is designated, for future reference, as signal "C."

The output of the filter 200 is applied to the negative input of a comparator amplifier 220, and the positive input of the amplifier 220 is connected to the wiper of threshold adjusting potentiometer 30 through resistor 222. Comparator amplifier 220 has an open collector output for positive input comparisons so that its output is normally set high through pull-up resistor 224. As the output of filter 200 increases above the voltage set by potentiometer 30, the output of comparator amplifier 220 goes low, thereby signaling the start of a muscle contraction. Resistor 226 provides the comparator amplifier 220 with hysteresis to prevent undesirable oscillation. The output of the comparator amplifier is identified for future reference as signal "D."

The signal "C" at the output of filter 200 is also applied to a unique logarithmic circuit 230. The input of logarithmic circuit 230 is applied to the summing junction of an operational amplifier 232 through summing resistor 234. The non-inverting input of amplifier 232 is connected to the wiper of a potentiometer 236 connected between positive and negative supply voltages by resistors 238,240, respectively. Potentiometer 236 is adjusted so that zero volts are applied to the non-inverting input of amplifier 232. Because of the high gain of amplifier 232, the summing junction of amplifier 232 is a virtual ground. Consequently, the current flowing through resistor 234 is directly proportional to the amplitude of the signal "C" applied to the input of logarithmic circuit 230. This current is equalized by the current flowing through a diode 242 connected in the feedback circuit of amplifier 232. The voltage across the diode 242, and hence the voltage at the output of amplifier 232, is equal to the sum of a constant and the logarithm of the current passing through the diode 242. Insofar as the current through the diode 242 is proportional to the amplitude of signal "C," the voltage at the output of amplifier 232 is equal to the sum of a constant and the logarithm of the amplitude of signal "C." Resistor 244 is provided to limit the gain of amplifier 232 when the diode 242 is not forward biased. Resistor 246 compensates for the input bias current to amplifier 232.

A fixed offset is applied to the output of amplfier 232 by amplifier 250 so that the output of amplifier 250 is directly proportional to the logarithm of the amplitude of signal "C" without the constant. Accordingly, the output of amplifier 232 is applied to the summing junction of amplifier 250 through resistor 252, and a feedback resistor 254 is connected between the output and summing junction of amplifier 250. The offset is applied to the non-inverting input of amplifier 250 through a potentiometer 256 which is connected to negative supply voltage by resistor 258. The output of amplifier 250 is connected to external circuitry through current-limiting resistor 260, and clipping diode 262 is provided to prevent negative outputs from being generated. The output of the logarithmic circuit 230 is identified for future reference as signal "F." As explained hereinafter, this signal is applied to the bar graphs 38,40,42,44 in the first operating mode.

Figure 3:
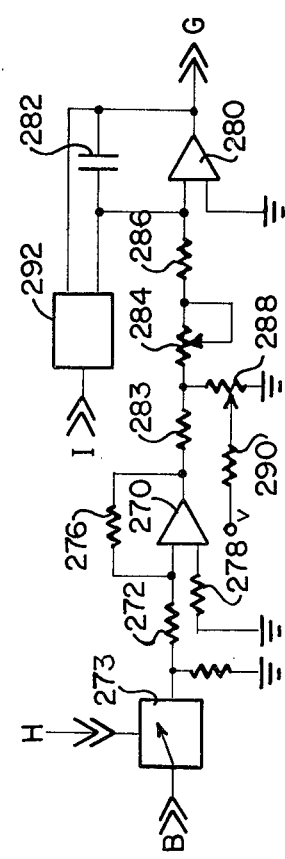
FIG. 3 is a schematic of a circuit for integrating the electromyograph signals during a number of muscle contractions.

With reference, now, to FIG. 3, the amplified, filtered and rectified signal "B" is applied to the summing junction of an operational amplifier 270 through a switch 273 and resistor 274 whenever the switch 273 is enabled by a signal "H," which, as explained hereinafter, is generated only during a muscle contraction. The gain of the amplifier 270 is set at unity by feedback resistor 276 being equal to resistor 274, and resistor 278 is provided to minimize the offset voltage from amplifier 270. The output of amplifier 270 is applied to the summing junction of a second operational amplifier 280 through resistor 283, potentiometer 284 and resistor 286. A potentiometer 288, having a wiper connected to supply voltage through resistor 290, is adjusted to compensate for the input bias current to amplifier 280 in order to prevent integration drift. A capacitor 282 is connected between the output and summing junction of amplifier 280 so that amplifier 280 functions as an integrator having an integration time constant determined by the capacitance of capacitor 282 and resistance of potentiometer 284. A switch 292 is connected across the capacitor 282 to discharge capacitor 282 responsive to a reset pulse which is generated as signal "I" when the switch 32 is actuated upwardly, as explained hereinafter. The output of the integrated amplifier 280, which is identified as signal "G," is thus a measure of the average amplitude of the signal from the electrodes 21 during a number of contractions.

The signal "D" at the output of comparator amplifier 220 is applied to an exclusive OR-gate 300 forming part of the digital processing circuitry illustrated in FIG. 5. The above-described circuitry is provided for each of the four electrode channels of the electromyograph. The circuitry described hereinafter, however, utilizes outputs from four electrode circuits, although the circuitry for a single electrode circuit is illustrated for purposes of clarity. Accordingly, it will be understood that the comparator amplifier outputs "D" for the remaining electrode circuits are also applied to exclusive OR-gates 300. The comparator amplifier outputs for the first, second and third channels "D1," "D2," "D3" are also applied to a NAND-gate 302 which also receives an input from NAND-gate 304 through inverter 306. NAND-gate 304, in turn, receives inputs from the comparator amplifier for channel 4 "D4" as well as a "CP-IN" signal. Accordingly, when any of the outputs from the comparator amplifiers 220 go low, the output of NAND-gate 302 goes high and is applied to the set inputs of four R-S flip-flops 308 through capacitor 310 and switch 312, which is closed in mode 3 in which muscle coordination is measured. The "Q" outputs of all flip-flops 308 then go low, thereby applying a low to the exclusive OR-gate 300 for each channel. Assuming, for example, that the threshold signal "D1" from channel 1 first goes low, a low is initially applied to one input of the exclusive OR-gate for channel 1. However, the flip-flops 308 for all channels are immediately set responsive to the threshold signal "D" for any channel going low. Consequently, the flip-flops 308 apply a low to their corresponding exclusive OR-gates 300. Insofar as the inputs to exclusive OR-gate 300 for channel 1 transition from "1,1" to "0,0," the output of the exclusive OR-gate 300 for channel 1 remains low. However, since a logic "0,1" is now being applied to the exclusive OR-gates 300 for the remaining channels, the outputs of the remaining exclusive OR-gates 300 go high and will remain high until the threshold signal "D" for each channel goes low. It can be seen, then, that the duration of the pulse at the output of each exclusive OR-gate 300 is equal to the time elapsing from contraction of the first-to-contract masticatory muscle to the contraction of the masticatory muscle for the channel with which the exclusive OR-gate 300 is associated. For example, if the threshold signal for the second channel "D2" first goes low, the output of the exclusive OR-gate 300 for channel 1 goes high since its inputs are then "0,1." However, when the threshold signal for channel 1 "D1" goes low, the inputs to exclusive OR-gate 300 will be "0,0," thereby causing the output of exclusive OR-gate 300 to once again go low.

After the contraction of each masticatory muscle terminates, the threshold signal "D" for each channel once again goes high, and this low-to-high transition is applied to the reset input of respective flip-flops 308 through capacitors 310. Accordingly, the inputs to the exclusive OR-gates 300 transition from "0,0" to "1,1" so that the output of the exclusive OR-gate 300 does not change. The flip-flops 308 for all channels are simultaneously reset by actuating the switch 32 upwardly to close reset switch 32A, thereby applying a logic "1" to all reset terminals through resistor 314.

The output of exclusive OR-gate 300 enables a 1 kHz clock signal to pass through NAND-gate 320 when NAND-gate 320 is enabled by a logic "1" at the output of flip-flop 322. Flip-flop 322 is set by the positive transition of exclusive OR-gate 300 through capacitor 324. Consequently, 1 kHz clock pulses cannot be gated through NAND-gate 320 except subsequent to the leading edge of a pulse from exclusive OR-gate 300. The 1 kHz clock pulses are generated by counter 326, which is driven by a 64 kHz oscillator 328 formed by NAND-gates 330,332 connected in a conventional manner. Other outputs of the counter 326 are used to generate 62 Hz, 125 Hz, 8 kHz, 16 kHz and 32 kHz clock pulses.

The output from NAND-gate 302 occurring upon the contraction of the first-to-contract masticatory muscle is also applied to the clock input of a counter 340 so that the counter 340 increments each time a contraction first occurs. The $Q_0$, $Q_1$ and $Q_3$ outputs of the counter 340 are applied to NAND-gate 342 to detect the eleven count, at which time the output of NAND-gate 342 goes low and removes the ENABLE from counter 340 so that counter 340 no longer increments. The low at the output of NAND-gate 342 also disables the NAND-gates 344 for each channel and the NAND-gates 346 for each channel. It will be remembered that the 1 kHz clock pulses are gated through the NAND-gates 320 for each channel, from the contraction of the first-to-contract muscle to the contraction of the muscle with which the NAND-gate 320 is associated. Consequently, these 1 kHz pulses are also gated through NAND-gate 344 and appear as a "Y" signal at the output of NAND-gate 344 during the contraction delays for a total of ten contractions. The signal "Y" at the output of the NAND-gates 344 for each channel is thus a measure of the contraction delay for the mandibular muscle associated with the channel during ten contractions. As explained in greater detail hereinafter, a digital indication of these signals is applied to the digital readouts 46,48,50,52 in the third operating mode.

As mentioned above, in any of the operating modes, digital indications corresponding to the interval between contractions for each channel are applied to digital readouts 54,56,58,60. Accordingly, the 1 kHz clock from counter 362 is gated through NAND-gates 350 for each channel when the NAND-gates are enabled by a logic "1" from respective flip-flops 322 and a logic "1" from the signal "D" at the output of the comparator amplifier 220. The threshold signal "D" is high between contractions so that NAND-gate 350 is enabled between contractions. The 1 kHz pulses at the output of NAND-gate 350 between contractions are applied to NAND-gate 346, which is enabled for the first ten contractions of the muscles.

The number of pulses generated at the output of the NAND-gates 346 for each channel is thus a measure of the interval between contractions for ten contractions. These pulses are applied to a combination counter-/analog-to-digital converter 352 through resistor 354 and attenuated by resistor 356. The reset signal from switch 32A resets the counter/analog-to-digital converter through resistor 358. The output of circuit 352 applied through resistors 360 is thus a voltage having a magnitude which is proportional to the average interval between contractions during ten contractions.

In the second and third modes, the switch 312 is open so that exclusive OR-gates 300 function merely as inverters. NAND-gates 320 are thus enabled during each contraction so that the 1 kHz pulses are gated through the NAND-gates 320 for each channel during the entire contraction. These pulses are gated through the NAND-gates 344 for each channel when enabled by NAND-gate 342 during the first ten contractions. Consequently, the number of pulses at "Y" is a measure of the average duration of the contractions during ten contractions. As explained above, digital indications of the duration of contractions are displayed in digital readouts 46,48,50,52 during the first and second operating modes.

The output of exclusive OR-gate 300 is also applied to a AND-gate 369, which is enabled during the first ten contractions by NAND-gate 342. The output of AND-gate 369 is the signal "H," which is used to switch the amplified, filtered and rectified signal to the integrator, as explained above. Consequently, integration occurs only during the first ten contractions.

A desirable feature of the mandibular electromyograph is the ability to test for masticatory muscle coordination, as explained above. Under some circumstances, it may be desirable to test muscle coordination with respect to more than four electrodes or with respect to an external stimulus. Accordingly, the external stimulus or a trigger signal from a second electromyograph is applied to NAND-gate 304 so that the "CP-IN" signal simulates the contraction of the first-to-contract muscle. The digital readouts 46,48,50,52 in the third operating mode then display the elapsed time between the start of the "CP-IN" signal and the contraction of each masticatory muscle with which the electrode circuit is associated. The output of NAND-gate 302, which goes high upon the contraction of the first-to-contract muscle, is inverted by inverter 380 and applied as a "CP-OUT" signal to the "CP-IN" ports of other electromyographs.

Figure 4:
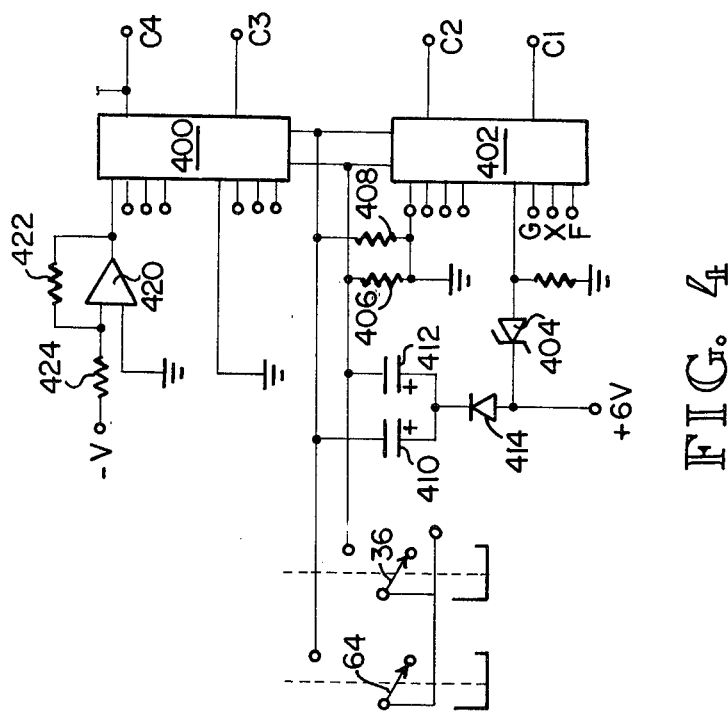
FIG. 4 is a schematic of a multiplexer for connecting various signals from the analog processing circuitry to the display circuitry.

The signals applied to the bar graphs 38,40,42,44 are mutiplexed by multiplexers 400,402 shown in FIG. 4. Wth reference to the channel 1 multiplexer 402, signals "G", "X" and "F," representing the integrated output from integration amplifier 280, the analog interval output from the counter/digital-to-analog converter 352, and logarithmic circuit output, respectively, are applied to inputs 2, 3 and 4 of the multiplexer 402. The positive supply voltage, reduced by zener diode 404, is applied to the first terminal of the multiplexer 402. The multiplexer 402 applies one of its four inputs to the channel 1 output "C1-OUT," depending upon the state of the control inputs A,B.

A "1,1" control input to the multiplexer 402 applies the supply voltage to the bar graph so that the condition of an internal supply battery can be determined. The "1,1" control input is automatically generated when power is initially applied to the electromyograph by actuating the power switch 34. Accordingly, the control inputs are normally held low through resistors 406,408. However, when power is initially applied to the system, supply voltage is applied to capacitors 410,412 through diode 414, thereby causing the control inputs A,B to go high. The high control inputs A,B the apply the anode of zener diode 404 to the "C1-OUT" output of the multiplexer 402 so that the battery voltage is displayed. After about three seconds, the capacitors 410,412 become sufficiently charged so that the control inputs A,B are "0,0," thereby disconnecting the anode of zener diode 404 from the output of multiplexer 402. The control inputs A,B are then determined by the position of mode switches 64,36. In mode 3, both switches 64,36 are open so that the control inputs A,B are "0,0," thereby causing the signal "F" from the output of the logarithmic circuit 230 to be applied to the output of multiplexer 402. In mode 2, switch 64 is closed, thereby applying a control signal "A,B" of "1,0" to the multiplexer 402, which connects the signal "X" from the output of the counter/digital-to-analog converter 352 to the output of multiplexer 402. Finally, in the first operating mode, the switch 36 is closed, while the switch 64 is open so that a control input A,B of "0,1" is applied to multiplexer 402. In this state, the signal "G" from the output of the integrating amplifier 280 is applied to the output of the multiplexer 402.

The multiplexer 400 for channels 3 and 4 functions in substantially the same manner as multiplexer 402. However, the negative supply voltage must be inverted by amplifier 420 having a gain set by resistors 422,424 since the bar graphs 38,40,42,44 respond only to positive voltages.

Figures 7, 8:
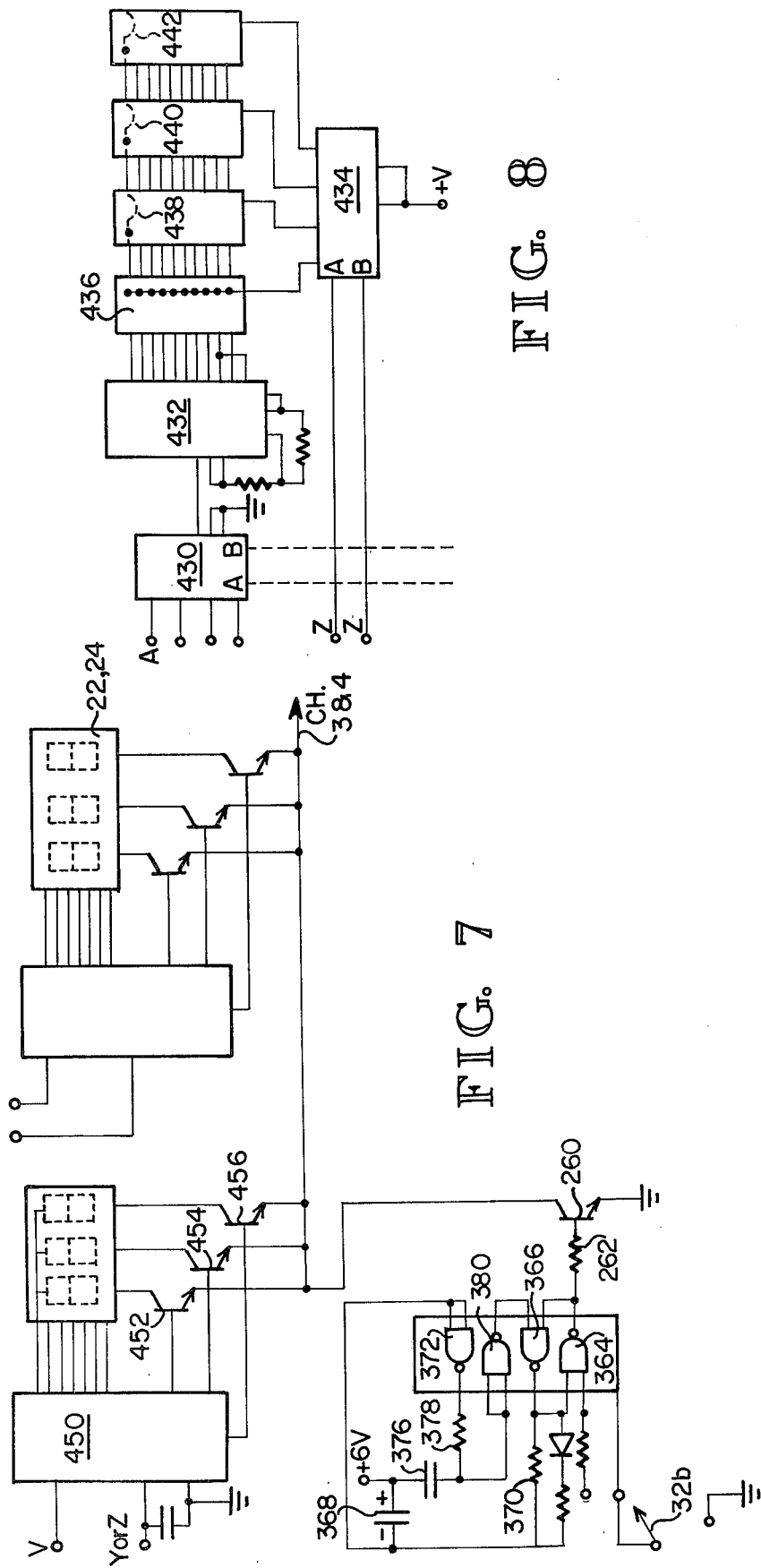
FIG. 7 is a schematic of the digital display circuitry.
FIG. 8 is a schematic of the analog display circuitry.

The outputs of the multiplexers 400,402 are applied to the analog display circuitry illustrated in FIG. 8. The outputs are received by a multiplexer 430 which is switched by the 62 Hz and 125 Hz outputs from counter 326. Thus the multiplex outputs for channels 1 through 4 are sequentially applied to a light-emitting diode bar graph driver 432 which applies a low to a number of its output lines, depending upon the amplitude of the incoming signal. The output lines of the driver 432 are connected to the light-emitting diodes of all bar graph displays. Each bar graph display is enabled by a multiplexer 434 which is driven by the same 62 Hz and 125 Hz clock signals from the counter 326. Thus, when the channel 1 input to multiplexer 430 is being applied to the driver 432, the bar graph 436 for channel 1 is enabled by multiplexer 434. Similarly, the bar graphs 438,440,442 are enabled in the same manner.

The pulses at the output of NAND-gate 344 identified as signal "Y," and the pulses at the output of NAND-gate 346, identified as signal "Z," are applied to respective counters 450 in the digital display circuit illustrated in FIG. 7. It will be remembered that the pulses "Y" are produced in the first and second operating modes during each contraction, and in the third operating mode, from the contraction of the first-tocontract muscle to the contraction of the muscle with which the channel is associated. The pulses "Z" are generated during the interval between contractions during ten contractions. The counters 450 produce seven LED segment outputs which drive the seven segments of all three digits of the digital readouts 46,48,50,52,54,56,58,60 in parallel. The counter 450 also produces enabling signals for each of the digits one at a time which are applied to the base of transistors 452,454,456. Counter 450 is enabled by the output which occurs until the eleventh contraction, so that counts occurring after the tenth contraction are not displayed. In operation, the pulses to be counted increment the counter 450 while the counter sequentially displays the count for three digits from the most significant digit to the least significant digit. The counter 450 is a four-digit device, but the outputs for the least significant digit are not used. This provides an automatic divide-by-ten so that the displayed output represents the average value for a single contraction, even though the counter has been incrementing during ten contractions.

The display circuitry explained above is enabled by a transistor 260 which is controlled by a timing circuit through resistor 262. When the switch 32 is actuated downwardly, switch 32B closes, thereby driving the output of NAND-gate 364 high, causing the output of NAND-gate 366 to go low, thereby discharging capacitor 368 through resistor 370. After capacitor 368 has been discharged sufficiently, the output of NAND-gate 372, acting as an inverter, goes high, thereby charging capacitor 376 through resistor 378. When capacitor 376 has charged sufficiently, the output of NAND-gate 380, acting as an inverter, goes low, causing the output of NAND-gate 366 to go high. Since switch 32B has since opened, the output of NAND-gate 364 then goes low, thereby cutting off transistor 260 and removing power to the display.

The mandibular electromyograph includes means for allowing the amplified, filtered and rectified signals from the electrodes 12 to be displayed in a manner which makes a pathological condition of the masticatory muscles readily apparent. The output signal "A" from each 60 Hz notch filter 142 is applied to a multiplexer 500 which is driven by the 8 kHz and 16 kHz clock signals from the counter 326. The multiplexer 500 thus applies each of the signals "A1"–"A4" to the summing junction of an operational amplifier 502 through resistors 504,506 having a gain determined by feedback resistor 508. At the same time, offset voltages determined by resistor divider network 510 are applied to the non-inverting input of amplifier 502 by multiplexer 512. Consequently, the signal for each electrode 12 is vertically displaced from the signal for the other electrodes 12 when the output of amplifier 502 is applied to an oscilloscope. A switch 514 connects resistors 516 to ground in all but the third operating mode so that the gain of the amplifier 502 is larger in the third operating mode because the signals from the electrodes 12 are generally reduced in amplitude. To compensate for this increased gain, the offset provided by the divider network 510 is also reduced by closing switch 518.

The multiplexed outputs "CH1" from the multiplexers 400,402 may also be displayed in a similar manner. Accordingly, the multiplexer outputs are applied to multiplexers 530,532 which are also driven by the 8 kHz and 16 kHz clock signals from the counter 326. The signal from multiplexer 530 is applied to the non-inverting terminal of amplifier 534, while the offset is applied by multiplexer 532 from divider network 536 to the summing junction of amplifier 534 through resistor 538 having a feedback resistance 540. Thus the channel 1 output is displayed a slight distance above the channel 2 output, which is displayed a slight distance above the channel 3 output, which is displayed a slight distance above the channel 4 output. As long as all masticatory muscles are well coordinated, the traces at the output of amplifier 534 will be substantially parallel. However, any lack of coordination will be readily apparent as the trace from one channel overlaps the trace of another channel.

I claim:

1. An electromyograph having a plurality of electrode channels receiving input signals from respective electrodes, each positioned to receive an electrical signal from a masticatory muscle, comprising:

threshold means for each electrode receiving respective input signals from said electrodes and generating respective actuating signals when the amplitude of said input signals exceeds a predetermined value;

first detector means receiving all of said actuating signals and generating an enabling signal for each electrode channel responsive to an actuating signal from any of said threshold means;

respective second detector means for each electrode channel, said second detector means terminating the enabling signal for said channel responsive to an actuating signal from the corresponding threshold means;

timer means for each electrode channel, said timer means recording the duration of the enabling signal for the corresponding electrode channel; and display means for each electrode channel receiving an output from the corresponding timer means indicative of the duration of the enabling signal for the corresponding electrode channel whereby said display means indicate the time elapsing between contraction of the first-to-contract masticatory muscle and the contraction of each of the remaining masticatory muscles.

2. The electromyograph of claim 1, further including means for applying an externally generated actuating signal to said first detector means so that said display means can provide an indication of the time elapsing between an external event and the contraction of each masticatory muscle.

3. The electromyograph of claim 2, further including means for applying the enabling signal from a first electromyograph to the first detector means of a second electromyograph such that a plurality of electromyographs may be used together to determine the coordination between a relatively large number of masticatory muscles.

4. The electromyograph of claim 1 wherein said first and second detector means comprise:

gating means receiving the acutating signals from all of said threshold means, said gating means generating a first control signal responsive to an actuating signal from any of said threshold means;

bistable multivibrator means for each electrode channel, the multivibrator means for all electrode channels being set by said first control signal while the multivibrator means for each electrode channel is individually reset responsive to termination of the actuating signal from the corresponding threshold means; and exclusive OR means for each electrode channel receiving the actuating signal from the corresponding threshold circuit and a set output signal from the corresponding bistable multivibrator means, said exclusive OR means generating said enabling signal when said actuating signal and the set output signal are either both present or both not present so that said exclusive OR means generates an enabling signal from the start of an actuating signal from the threshold means of any electrode channel until the start of an actuating signal from the threshold means of the corresponding electrode channel.

5. The electromyograph of claim 4 wherein said timer means comprise:
  oscillator means for generating a clock signal having a predetermined frequency;
  second gating means receiving said clock signal, said gating means enabled by the enabling signal from the exclusive OR means of the corresponding electrode channels; and
  counter means having its input connected to the output of said second gating means so that said second counter means is incremented by said clock signal during said enabling signal, whereby the contents of said counter indicate the duration of said enabling signal.

6. The electromyograph of claim 4, further including means for selectively disconnecting the output of said gating means from said bistable multivibrator means so that said enabling signal is produced during the entire duration of said actuating signal, whereby said display means provides an indication of the duration of said actuating signal.

7. The electromyograph of claim 4, further comprising:
  counter means having its clock input connected to the output of said gating means so that said counter means is incremented by the first-to-be-generated actuating signal from all of said threshold means;
  decoder means receiving the output of said counter means for generating a disabling signal responsive to said counter means incrementing to a predetermined value; and
  switch means for disconnecting said enabling signal from said timer means responsive to said disabling signal so that said timer means records the duration of said enabling signal for a predetermined number of actuating signals.

8. The electromyograph of claim 1, further including:
  integrator means for generating an output signal which is the integral with respect to time of each input signal;
  switch means actuated by said actuating signal for applying the input signal to said integrator means such that the input signal is integrated only when said input signal exceeds said predetermined value; and
  display means for producing an indication of the amplitude of said integrator means output signal.

9. The electromyograph of claim 8, further including means for counting the number of actuating signals applied to said switch means and preventing said actuating signal from actuating said switch after said count reaches a predetermined value, whereby said input signals are integrated over several muscle contractions.

10. An electromyograph receiving an input signal from an electrode positioned to receive an electrical signal from a masticatory muscle, comprising:
  threshold means receiving said input signal from said electrode and generating an actuating signal when the amplitude of said input signal exceeds a predetermined value;
  integrator means for generating an output signal which is the integral with respect to time of a signal applied to its input;
  switch means actuated by said actuating signal for applying the input signal from said electrode to said integrator means such that the electrode signal is integrated only when said input signal exceeds said predetermined value; and
  display means for producing an indication of the amplitude of said integrator means output signal.

11. The electromyograph of claim 10, further including means for counting the number of actuating signals applied to said switch means and preventing said actuating signals from actuating said switch after said count reaches a predetermined value, whereby said input signals are integrated over several muscle contractions.

12. An electromyograph receiving an input signal from an electrode positioned to receive an electrical signal from a masticatory muscle, comprising:
  threshold means receiving said input signal from said electrode and generating an actuating signal when the amplitude of said input signal exceeds a predetermined value;
  first counter means incremented by said actuating signal and providing an enabling signal until said counter means has incremented to a predetermined number of contractions;
  first gating means receiving a clock signal, said gating means being enabled by said actuating signal to apply said clock signal to its output during each muscle contraction;
  second gating means receiving the output of said first gating means, said gating means being enabled by said enabling signal to apply said clock signal to its output during each muscle contraction;
  counter means incremented by the output of said second gating means; and
  display means for displaying the contents of said counter, thereby displaying the duration of a predetermined number of muscle contractions.

13. An electromyograph receiving an input signal from an electrode positioned to receive an electrical signal from a masticatory muscle, comprising:
  threshold means receiving said input signal from said electrode and generating an actuating signal when the amplitude of said input signal is less than a predetermined value;
  first counter means incremented by said actuating signal and providing an enabling signal until said counter means has incremented to a predetermined number of contractions;
  first gating means receiving a clock signal, said gating means being enabled by said actuating signal to apply said clock signal to its output between each muscle contraction;
  second gating means receiving the output of said first gating means, said gating means being enabled by said enabling signal to apply said clock signal to its output between each muscle contraction;
  counter means incremented by the output of said second gating means; and
  display means for displaying the contents of said counter, thereby displaying the interval between said predetermined number of muscle contractions.

14. In an electromyograph device for measuring and displaying an electrical signal generated by a masticatory muscle picked up by an electrode and multiplied in amplitude by an amplifier means, a zero-offset, full-wave rectifier, comprising:
- a first operational amplifier having an inverting input, a non-inverting input, an output voltage proportional to the voltage between said inverting and non-inverting inputs and a relatively high impedance between said inverting and non-inverting inputs;
- a second operational amplifier having an inverting input, a non-inverting input, an output voltage proportional to the voltage between said inverting and non-inverting inputs and a relatively high impedance betwen said inverting and non-inverting inputs;
- first impedance means connecting said amplified electrical signal to the inverting terminal of said first amplifier means;
- second impedance means connected between the output and inverting input of said first amplifier means;
- third impedance means interconnecting the noninverting terminals of said first and second operational amplifier;
- fourth impedance means connecting the output of said first operational amplifier to the inverting input of said second operational amplifier;
- fifth impedance means having an impedance substantially equal to the impedance of said fourth impedance means connecting the output and inverting input of said second operational amplifier;
- first and second diodes having like terminals connected to each other, the remaining terminal of said first diode being connected to the output of said first operational amplifier and the remaining terminal of said second diode being connected to the output of said second oprational amplifier;
- a third diode connected between the non-inverting terminal of said second operational amplifier and a fixed voltage, with like terminals of said second and third diodes being connected to the output and non-inverting input, respectively, of said second operational amplifier; and
- bias means for directing a current through said third diode, which is adjusted so that the voltage on the non-inverting input of said second operational amplifier is equal to the voltage at the output of said first and second operational amplifiers, whereby said first diode immediately conducts current responsive to a negative electrical signal from said electrode and said second diode immediately conducts current responsive to a positive electrical signal from said electrode.

15. In an electromyograph device having a plurality of electrode channels receiving input signals from respective electrodes each positioned to receive an electrical signal from a masticatory muscle, said electromyograph producing from said input signals respective output signals indicative of a characteristic of said input signals, means for combining said output signals in a manner that facilitates comparison of said output signals, comprising:
- a differential amplifier providing an output signal having an amplitude which is proportional to the differential voltage applied between a pair of input terminals;
- first multiplexer means receiving said output signals and sequentially connecting said signals to one input of said differential amplifier input terminals;
- means for providing a plurality of offset voltages corresponding in number to the number of output signals generated by said electromyograph; and
- second multiplexer means operating in synchronism with said first multiplexer means, said second multiplexer means receiving said offset signals and sequentially applying said signals to the other input of said differential amplifier so that an oscilloscope may be connected to the output of said differential amplifier for displaying said output signal, and said output signals normally form a uniform pattern in which said signals track substantially parallel to each other but form a non-uniform pattern in which signals overlap each other in an abnormal condition, thus making abnormal characteristics of said masticatory muscles readily apparent.

16. An electromyograph having a plurality of electrode channels receiving input signals from respective electrodes each positioned to receive an electrical signal from a masticatory muscle, comprising:
- respective amplifier means connected to said electrodes for increasing the amplitude of said input signals;
- first filter means connected to the output of each amplifier means for modifying the frequency characteristics of said input signals;
- rectifier means connected to the output of each first filter means for providing respective rectified signals which are proportional to the absolute value of the signal from said filter means;
- second filter means connected to the output of each rectifier means for removing relatively high-frequency components from said rectified signal;
- threshold means connected to the output of said second filter means for generating respective actuating signals responsive to the amplitude of said filtered rectified signals exceeding a predetermined value;
- logarithmic circuit means connected to the output of each second filter means for generating a logarithmic output signal which is proportional to the logarithm of the amplitudes of the filtered rectified signals;
- integrator means for each electrode channel generating an integrator output signal having a magnitude which is proportional to the integral with respect to time of a signal applied to its input;
- first switch means for connecting the output of said rectifier means to said integrator means responsive to said actuating signal;
- processor means connected to each threshold means for generating a processor output signal indicative of a time-related characteristic of said actuating signal;
- analog display means for each channel, providing an indication of the amplitude of a signal applied to its input; and
- second switch means for selectively connecting either the log output signal, integrator output signal, or processor output signal to said analog display means.

17. The electromyograph device of claim 16, further comprising:
- threshold means for each electrode receiving respective input signals from said electrodes and generating respective actuating signals when the amplitude of said input signals exceeds a predetermined value;

first detector means receiving all of said actuating signals and generating an enabling signal for each electrode channel, responsive to an actuating signal from any of said threshold means;

respective second detector means for each electrode channel, said second detector means terminating the enabling signal for said channel responsive to an actuating signal from the corresponding threshold means;

timer means for each electrode channel, said timer means recording the duration of the enabling signal for the corresponding electrode channel; and digital display means for each electrode channel receiving an output from the corresponding timer means indicative of the duration of the enabling signal for the corresponding electrode channel whereby said display means indicate the time elapsing between contraction of the first-to-contract masticatory muscle and the contraction of each of the remaining masticatory muscles.

18. The electromyograph of claim 16 wherein said first and second detector means comprise:

gating means receiving the actuating signals from all of said threshold means, said gating means generating a first control signal responsive to an actuating signal from any of said threshold means;

bistable multivibrator means for each electrode channel, the multivibrator means for all electrode channels being set by said first control signal while the multivibrator means for each electrode channel is individually reset responsive to termination of the actuating signal from the corresponding threshold means; and exclusive OR means for each electrode channel receiving the actuating signal from the corresponding threshold circuit and a set output signal from the corresponding bistable multivibrator means, said exclusive OR means generating said enabling signal when said actuating signal and the set output signal are either both present or not present so that said exclusive OR means generates an enabling signal from the start of an actuating signal from the threshold means of any electrode channel until the start of an actuating signal from the threshold means of the corresponding electrode channel.

19. The electromyograph of claim 16 wherein said rectifier means comprise:

a first operational amplifier having an inverting inout, a non-inverting input, an output voltage proportional to the voltage between said inverting and non-inverting inputs and a relatively high impedance between said inverting and non-inverting inputs;

a second operational amplifier having an inverting input, a non-inverting input, an output voltage proportional to the voltage between said inverting and non-inverting inputs and a relatively high impedance between said inverting and non-inverting inputs;

first impedance means connecting said amplified electrical signal to the inverting terminal of said first amplifier means;

second impedance means connected between the output and inverting output of said first amplifier means;

third impedance means interconnecting the noninverting terminals of said first and second operational amplifier;

fourth impedance means connecting the output of said first operational amplifier to the inverting input of said second operational amplifier;

fifth impedance means having an impedance substantially equal to the impedance of said fourth impedance means connecting the output and inverting input of said second operational amplifier;

first and second diodes having like terminals connected to each other, the remaining terminal of said first diode being connected to the output of said first operational amplifier and the remaining terminal of said second diode being connected to the output of said second operational amplifier;

a third diode connected between the non-inverting terminal of said second operational amplifier and a fixed voltage, with like terminals of said second and third diodes being connected to the output and non-inverting input, respectively, of said second operational amplifier; and bias means for directing a current through said third diode, which is adjusted so that the voltage on the non-inverting input of said second operational amplifier is equal to the voltage at the output of said first and second operational amplifiers, whereby said first diode immediately conducts current responsive to a negative electrical signal from said electrode and said second diode immediately conducts current responsive to a positive electrical signal from said electrode.

20. The electromyograph of claim 16 wherein said logarithmic circuit means comprise:

an operational amplifier having an inverting input, a non-inverting input, an output voltage proportional to the voltage between said inverting and non-inverting inputs, and a relatively high impedance between said inverting and noninverting inputs;

first impedance means connecting to said non-inverting input to a fixed voltage;

second impedance means connecting said electrical signal to said inverting input; and a diode connected between said inverting input and said output such that the current through said second impedance is proportional to the amplitude of said electrical signal and is substantially equal to the current through said diode, whereby the amplitude of the signal at said output is proportional to the logarithm of said electrical signal.

* * * * *